United States Patent
Muraca et al.

(10) Patent No.: US 10,881,611 B2
(45) Date of Patent: Jan. 5, 2021

(54) EXTRACELLULAR VESICLES DERIVED FROM OSTEOBLASTIC LINEAGE CELLS FOR THERAPEUTIC AND DIAGNOSTIC USE

(71) Applicant: Fondazione Città Della Speranza—Onlus, Monte di Malo (VI) (IT)

(72) Inventors: Maurizio Muraca, Padua (IT); Alfredo Cappariello, L'Aquila (IT); Anna Maria Teti, L'Aquila (IT)

(73) Assignee: Fondazione Città Della Speranza—Onlus, Monte di Malo (VI) (IT)

( * ) Notice: Subject to any disclaimer, the term of this patent is extended or adjusted under 35 U.S.C. 154(b) by 0 days.

(21) Appl. No.: 15/737,144

(22) PCT Filed: Jun. 16, 2016

(86) PCT No.: PCT/IB2016/053562
§ 371 (c)(1),
(2) Date: Dec. 15, 2017

(87) PCT Pub. No.: WO2016/203414
PCT Pub. Date: Dec. 22, 2016

(65) Prior Publication Data
US 2018/0193263 A1 Jul. 12, 2018

(30) Foreign Application Priority Data
Jun. 16, 2015 (IT) .................. IT102015000024334

(51) Int. Cl.
| | | |
|---|---|---|
| C12N 15/11 | (2006.01) |
| A61K 9/127 | (2006.01) |
| A61K 35/32 | (2015.01) |
| A61K 31/282 | (2006.01) |
| A61K 31/7048 | (2006.01) |
| A61K 31/675 | (2006.01) |
| A61K 31/519 | (2006.01) |
| A61K 31/704 | (2006.01) |
| A61K 31/555 | (2006.01) |
| A61P 35/00 | (2006.01) |
| C12N 5/077 | (2010.01) |
| A61K 31/7088 | (2006.01) |
| A61K 31/7105 | (2006.01) |
| A61K 31/351 | (2006.01) |
| A61K 31/401 | (2006.01) |
| A61K 31/435 | (2006.01) |
| A61K 31/55 | (2006.01) |
| A61K 33/24 | (2019.01) |

(52) U.S. Cl.
CPC ............ *A61K 9/127* (2013.01); *A61K 31/282* (2013.01); *A61K 31/519* (2013.01); *A61K 31/555* (2013.01); *A61K 31/675* (2013.01); *A61K 31/704* (2013.01); *A61K 31/7048* (2013.01); *A61K 35/32* (2013.01); *A61P 35/00* (2018.01); *C12N 5/0654* (2013.01); *A61K 31/351* (2013.01); *A61K 31/401* (2013.01); *A61K 31/435* (2013.01); *A61K 31/55* (2013.01); *A61K 31/7088* (2013.01); *A61K 31/7105* (2013.01); *A61K 33/24* (2013.01); *A61K 2300/00* (2013.01)

(58) Field of Classification Search
CPC ..................................... A61K 9/127
See application file for complete search history.

(56) References Cited

U.S. PATENT DOCUMENTS

| | | | | |
|---|---|---|---|---|
| 2003/0068307 A1* | 4/2003 | Yu | ............ | A61K 31/7048 424/93.21 |
| 2003/0148454 A1* | 8/2003 | Marshak-Rothstein | ............ | C07K 14/70575 435/69.1 |
| 2007/0243137 A1 | 10/2007 | Hainfeld | | |

FOREIGN PATENT DOCUMENTS

| | | |
|---|---|---|
| WO | WO 2011/097480 A1 | 8/2011 |
| WO | WO 2011/128424 A1 | 10/2011 |
| WO | WO 2013/169202 A1 | 11/2013 |
| WO | WO 2014/141683 A1 | 9/2014 |

OTHER PUBLICATIONS

Kariya et al, Vps33a Mediates RANKL Storage in Secretory Lysosomes in Osteoblastic Cells, 2009, Journal of Bone and Mineral Research, vol. 24, 10: 1741-1752.*

Chen et al, Expression of RANKL/RANK/OPG in Primary and Metastatic Human Prostate Cancer as Markers of Disease Stage and Functional Regulation, Cancer, 2006, vol. 107, 2: 289-298 (Year: 2006).*

Jules et al, Selective targeting of RANK signaling pathways as new therapeutic strategies for osteoporosis, Expert Opinion on Therapeutic Targets, 2010, 14:9, 923-934 (Year: 2010).*

International Search Report for International Application No. PCT/IB2016/053562, International Searching Authority, United States, dated Sep. 27, 2016, 16 pages.

(Continued)

*Primary Examiner* — Ekaterina Poliakova-Georgantas
(74) *Attorney, Agent, or Firm* — Sterne, Kessler, Goldstein & Fox P.L.L.C.

(57) ABSTRACT

The present invention relates to RANKL+ cellular vesicles isolated from osteoblastic lineage cells, optionally immortalised, their use for the therapeutic treatment of bone pathologies and for diagnostic purposes, and processes for the production of said vesicles.

2 Claims, 8 Drawing Sheets

(56) References Cited

OTHER PUBLICATIONS

Shimbo, K., et al.,"Exosome-formed synthetic microRNA-143 is transferred to osteosarcoma cells and inhibits their migration," *Biochemical and Biophysical Research Communications* 445 (2014) 381-387, Elsevier B.V., Netherlands (available online Feb. 10, 2014).

Yang, C., et al., "Immunosuppressive Exosomes: A New Approach for Treating Arthritis," *International Journal of Rheumatology* 2012:573528, Hindawi Publishing Corporation, Egypt (2012), 9 pages.

Pascucci, L., et al., "Paditaxel is incorporated by mesenchymal stromal cells and released in exosomes that inhibit in vitro tumor growth: A new approach for drug delivery." *Journal of Controlled Release* 192 (2014) 262-270, Elsevier B.V., Netherlands (available online Jul. 30, 2014).

Morhayim, J., et al., "Proteomic signatures of extracellular vesicles secreted by nonmineralizing and mineralizing human osteoblasts and stimulation of tumor cell growth," *The FASEB Journal* 29(1):274-85, The Federation of American Societies for Experimental Biology, United States (Oct. 30, 2014).

Hoshino, A., et al., "Tumour exosome integrins determine organotropic metastasis," Nature 527(7578):329-335, Nature Publishing Group, United Kingdom (2015).

Wiklander, O., et al., "Extracellular vesicle in vivo biodistribution is determined by cell source, route of administration and targeting," Journal of Extracellular Vesicles 4:26316, Co-action Publishing, Scandinavia (2015).

Jan, A.T., et al., "Biology, Pathophysiological Role, and Clinical Implications of Exosomes: A Critical Appraisal," *Cells* 2019, 8, 99, MDPI Switzerland (2019).

Deng, L., et al., "Osteoblast-derived microvesicles: A novel mechanism for communication between osteoblasts and osteoclasts," *Bone* 79:37-42, Elsevier Inc., Netherlands (2015).

"Programme & Abstract Book—Exosomes in Pathological Conditions: new insights for biomarker development and therapeutic applications," Proceedings from the *AICC—Associazione Italiana Colture Cellulari* (Jun. 9-10, 2016), Italy, 31 pages.

\* cited by examiner

EXTRACELLULAR VESICLES DERIVED FROM OSTEOBLASTIC LINEAGE CELLS FOR THERAPEUTIC AND DIAGNOSTIC USE

PRIORITY

This application is a National Stage of International Application No. PCT/IB2016/053562, filed Jun. 16, 2016, which claims the priority benefit of Italian Application No. 102015000024334, filed Jun. 16, 2015, each of which is hereby incorporated by reference herein in its entirety.

The present invention relates to cellular vesicles isolated from osteoblastic lineage cells, optionally immortalised, characterized by the presence of RANKL membrane protein, their use for the therapeutic treatment of bone pathologies and for diagnostic purposes, and processes for the production of said vesicles.

PRIOR ART

Recent evidence demonstrated how intercellular communication can occur by release of extracellular vesicles (EVs), which carry therein transcriptional and/or protein information of the cell of origin. EVs are vesicles containing membrane-coated cytoplasm portions, released from cells in the microenvironment. Therefore, EVs summarize the original cells features mirroring the molecular and biological peculiarity of the cells, as they can comprise exclusive markers and molecules of a specific cell lineage, which is a characteristic that encourages to consider said EVs as a "liquid biopsy" of a physio-pathological situation. These vesicles represent a heterogeneous population comprising exosomes and microvesicles, that can be told apart based on size, antigen composition and secretion modes and that can vehiculate different biological information.

It is known that EVs can directly stimulate target cells, by receptor-ligand interaction, or can transfer ligands, receptors, proteins, nucleic acids and even mitochondria.

It is also known that EVs are involved in numerous diseases and take part in immunoregulation and tissue regeneration. By virtue of this molecular makeup, EVs are able to induce in target cells a "reprogramming" effect following integration with the transcriptomic machinery and/or by activating membrane receptors.

Numerous studies have demonstrated EV ability to induce tissue and organ regeneration in animal models of human diseases (Bruno et al., 2009; Lai et al., 2010; van Poll et al., 2008; Zhang et al., 2012).

Other studies have demonstrated the possibility of loading EVs with medicaments, thereby ameliorating the transfer of therapeutic molecules inside the target cells Shimbo et al., 2014. Also "first-in-man" studies have been published which employ EVs derived from some cell species (dendritic cells, mesenchymal stem cells) in human pathologies, demonstrating clinical applicability and providing preliminary evidence on therapeutic potentials of these complex extracellular particles (Kordelas et al., 2014; Le Pecq, 2005; Morse et al., 2005).

Very recently, the production of EVs from cells of osteoblastic lineage has been described (Morhayim et al., 2015), the protein composition and the interaction with cell lines of prostatic carcinoma thereof being described. To note that in this paper the presence of RANKL protein has not been disclosed. It does not appear that EVs isolated from osteoblasts have been characterised by the presence of RANKL, nor used with this characteristic for medical or diagnostic use.

As known, the (Receptor activator of nuclear Factor kappa B Ligand) known also as TNFSF11, TRANCE, OPGL, ODF is the key cytokine for the osteoclastogenesis and osteoclast maturation process (the absence of RANKL in man results in severe pathology with unfavourable outcome, known infantine recessive osteopetrosis) and of thymus maturation and development. This cytokine is also involved in the maturation process of the glandular epithelium, in particular of the mammary epithelium. The protein is therefore involved in the said "vicious circle" of numerous skeletal pathologies such as rheumatoid arthritis, multiple myeloma and secondary metastatic lesions from prostatic and breast tumours. On the tumour aspect, RANKL supports the metastatic development, as it triggers osteoclastic activity, and also induces the tumour growth, as some tumours, such as breast tumours, can express RANK receptor, involved in the cellular proliferation and survival.

Given the seriousness and the difficulties of treatment of numerous bone pathologies, tumours and bone metabolic alterations included, the development of clever vehicles (carriers), agents for the treatment of bone pathologies, is of constant interest.

SUMMARY OF THE INVENTION

The present invention relates to extracellular vesicles characterised by the presence of RANKL on the membrane isolated from osteoblastic lineage cells (RANKL+ O-EVs), optionally immortalised, as carriers of drugs for the treatment of bone tumours, bone infections and bone metabolic alterations. In particular, the invention relates to the use of RANKL+ O-EVs as clever carriers of drugs, able to selectively concentrate them in osteoblastic line cells, the main agents in charge of bone formation and remodelling, as well as of the most relevant neoplastic diseases of bone.

The Authors of the present invention have in fact discovered that particular EVs can be isolated from culture media of mammal primary osteoblasts and from osteoblastic lineage cells, optionally immortalised and have identified, as evident from the experiments, a EVs subpopulation characterised by the presence of the membrane cytokine RANKL presence as defined above. The authors have also found the way to increase the percentage of the RANKL+ EVs population by pretreatment of osteoblasts with perithyroidal hormone, or, additionally, by genetical engineering modification of the cells from which said vesicles are isolated, in order to overexpress RANKL in said cells The Authors of the present invention have moreover demonstrated that RANKL+ O-EVs are able to intervene in cellular phenomena regulating bone metabolism, and to influence bone cell formation and function. In fact, when administered to mature osteoblasts O-EV can increase the osteoclast parameters. In addition, the Inventors have found that, by exploiting RANKL+ O-EV properties, it is possible to modify pathological functions intrinsic to bone tissue, corroborating the highly specific therapeutic potential of RANKL+ O-EVs. Therefore, RANKL+ O-EVs can be advantageously employed as carrier of anti-tumour drugs, both for primitive bone tumours, and for tumours metastasized to bone. Moreover, RANKL+ O-EVs can be utilized to specifically carry inside the osteoblast and osteoclast biological molecules (e.g., cytokines) and drugs for the treatment of bone metabolism disorders. In particular, the Authors of the invention have observed that RANKL+ O-EVs have a marked osteotropism in vivo. The Authors have demonstrated, by confocal microscopy in parietal bone organ cultures, that RANKL+ O-EVs are captured (uptaken)

and integrated in bone tissue, in support of an advantageous use thereof in the specific therapeutic treatment of skeletal diseases. This in vitro and in vivo targeting specificity of the RANKL+ O-EVs has never been described previously.

Furthermore, the Authors of the invention have demonstrated that administration of RANKL+ O-EV-encapsulated anti-tumour drugs results in a 100-fold enhancement of drug effectiveness, as compared to administration of the free drug. The vesicles of the invention are also capable of vehiculating bone reabsorption inhibiting agents, such as medicaments belonging to the N-bisphosphonates class such as zoledronate.

Therefore, object of the present invention are:

extracellular vesicles that are RANKL positive (i.e. characterised by the presence of RANKL on the membrane) isolated from osteoblastic lineage cells, optionally immortalised, for use in the therapeutic treatment of bone pathologies, optionally loaded with therapeutic agents, pharmaceutical compositions comprising said vesicles and at least one pharmacologically acceptable excipient, a process for the preparation of extracellular vesicles isolated from osteoblastic lineage cells, optionally immortalised, comprising the steps of:

a. culturing osteoblastic lineage cells, optionally immortalised b. collecting, by ultrafiltration and/or ultracentrifugation, the extracellular vesicles produced by the cultured cells; and c. selecting the RANKL positive (RANKL+) veshicles.

Further objects of the invention are a process for loading extracellular vesicles isolated from osteoblastic lineage cells, optionally immortalised, with one or more therapeutic agents or with one or more contrast agents, comprising the steps of a. incubating said vesicles and/or osteoblastic lineage cells, optionally immortalised, in a culture media containing said one or more therapeutic agents or one or more contrast agents b. collecting by ultracentrifugation and/or filtration and/or ultrafiltration and/or column filtration, ultracentrifugation on sucrose gradient and/or separation of the RANKL+ vesicles with immunomagnetic methods;

a process for loading extracellular vesicles isolated from osteoblasts osteoblastic lineage cells, optionally immortalised, with one or more therapeutic agents, comprising the steps of a. transforming osteoblastic lineage cells, optionally immortalised, so to express a therapeutic agent of interest, b. culturing immortalised osteoblasts or osteoblastic cells of the osteoblastic lineage, optionally immortalised, transformed in step a., c. collecting by ultracentrifugation and/or ultrafiltration and/or column filtration, ultracentrifugation on sucrose gradient and/or separation with immunomagnetic methods the vesicles thus loaded, extracellular vesicles isolated from osteoblastic lineage cells, optionally immortalised, obtainable with one of the above-described processes;

a therapeutic method for the treatment of bone pathologies, comprising the administration of therapeutically effective doses of said extracellular vesicles, optionally loaded with one or more therapeutic agents; and the use of the RANKL+ O-EV vesicles according to the invention, loaded with contrast agents, as biological markers for imaging techniques for the diagnosis of bone pathologies.

Glossary

The meanings of some terms are provided herebelow; said meanings apply to the entire description, unless specified otherwise.

The term "extracellular vesicles" is to be understood with the meaning commonly used in scientific literature, and refers to vesicles containing membrane-coated cytoplasm portions, released from cells in the microenvironment. These vesicles represent a heterogeneous population comprising exosomes and microvesicles, which can be told apart based on size, antigen composition and secretion modes.

These vesicles represent a heterogeneous population comprising exosomes and microvesicles, that can be told apart based on size, antigen composition and secretion modes.

"Loaded" extracellular vesicles, or "load extracellular vesicles" means, for the purposes of the present invention, that the vesicles comprise, inside them and/or on their surface, therapeutic agents of interest normally not present therein.

By "therapeutically effective dose" it is meant that amount of active compound or of therapeutic agent inducing a biological or medical response in an animal or human tissue system desired by the researcher, veterinary, general practitioner or other physician, comprising the palliation of symptoms of the disease or disorder treated.

As used herein, by the term "composition" it is meant a product comprising the specific ingredients in the specific amounts, as well as any product resulting, directly or indirectly, from the combination of the specific ingredients in the specific amounts.

In order to provide a more concise description, some of the quantitative expressions given herein are not qualified with the term "about". Evidently, regardless of an explicit use or absence of an explicit use of the term "about", any amount given herein is meant as referred to the given value, and is also meant as referred to an approximation of said given value that would reasonably have been inferred by a person of ordinary skill in the art, including approximations due to experimental and/or measuring conditions for said given value.

The term "subject" as used herein refers to an animal, preferably a mammal, more preferably a human being, who has been subject of treatment, observation or experiment.

The term "therapeutic agents" as used herein comprises agents with pharmacological effects inducing a biological or medical response in an animal or human tissue system desired by the researcher, veterinary, general practitioner or other physician, comprising the palliation of the symptoms of the disease or disorder treated; said agents can be chemical compounds, biological molecules with therapeutic activity (e.g., siRNAs, miRNAs, anti-miRNAs, shRNAs, etc., antibodies, antibody fragments recognizing specific epitopes), anti-tumour drugs, radiotherapy drugs.

The terminology "osteoblastic lineage cells, optionally immortalised" as used herein refers to osteoblasts or osteoblastic cells immortalised by genetic manipulations.

The term "contrast agents" as used herein comprises agents that can be visualized by diagnostic imaging techniques such as, e.g., radiopaque or radioactive contrast agents (e.g., iodate compounds, radioactive isotopes) or paramagnetic ones for nuclear magnetic resonance (e.g., gadolinium chelated compounds).

RANKL stands for Tumor necrosis factor ligand superfamily member 11, indicated on SWISSPROT also with the alternative names: Osteoclast differentiation factor (ODF); Osteoprotegerin ligand (OPGL); Receptor activator of nuclear factor kappa-B ligand (RANKL); TNF-related activation-induced cytokine (TRANCE); CD_antigen: CD254 and mammalian homologues thereof.

DETAILED DESCRIPTION OF THE FIGURES

FIG. 1 shows FACS (FACSCalibur—BD) evaluation of RANKL+ O-EV pellets isolated from osteoblast conditioned medium. In A, instrument calibration by commercial microparticles (Spherotech) of known size (0.25-0.54-0.79-1.25 micrometres) is shown; in B, the point graph deriving from vesicular pellet evaluated for CMFDA positivity and size is shown, the size window for subsequent analysis is plotted. In C, carboxymethyl fluorescein diacetate (CMFDA) positive (left) and CMFDA/Phycoerythrin (PE) positive (right) RANKL+ O-EV populations are shown. In D and F, CMFDA positive (left) and CMFDA/PE positive (right) RANKL+ O-EV populations of RANKL+ O-EVs isolated from osteoblasts treated with vehicle (D) or with $10^{-8}$ M human recombinant parathyroid hormone (E) are compared. In F the quantification of the RANKL+ O-EVs produced by primary osteoblast percent.

DETAILED DESCRIPTION OF THE INVENTION

The Authors of the present invention have, as mentioned above, demonstrated that it is possible to isolate extracellular vesicles (O-EVs) from osteoblastic lineage cells, optionally immortalised, and that said vesicles thus isolated can be used for therapeutic purposes.

The invention therefore relates to extracellular vesicles isolated from osteoblastic lineage cells, optionally immortalised, for use in the therapeutic treatment of bone pathologies.

The O-EVs of the invention can be used in the therapeutic treatment of any animal having a bone endoskeleton, in particular mammals, in particular humans.

The vesicles object of the invention can therefore be isolated from osteoblastic lineage cells, optionally immortalised, of any animal having a bone endoskeleton.

In one embodiment, O-EVs are isolated from mammalian cells. In a specific embodiment, the O-EVs of the invention are isolated from human cells.

As to the pathologies that can be treated with the RANKL+ O-EVs of the invention, the Authors have demonstrated (see Examples 1 and 2 and related figures) that the RANKL+ O-EVs of the invention can be used, for instance, for the treatment of osteopetrosis induced by RANKL (Receptor Activator of NF-κB Ligand) deficit in murine models.

In fact, the Authors have verified that cells in charge of RANKL production, a protein needed for osteoclastogenesis process, accountable for bone remodelling, can release EVs that transfer biological information to target cells (e.g., monocytes and osteoclasts). Data obtained on murine models demonstrate that this mechanism can be used as therapeutic instrument for the treatment of patients affected by osteopetrosis induced by RANKL deficit, in view of the fact that to date there is no therapeutic approach and that they survive for some years in strongly compromised conditions.

The Authors of the invention have isolated RANKL+ O-EVs by ultracentrifugation from culture medium of primary osteoblasts of murine parietal bones. In this population, the Authors have identified a RANKL-positive EV subpopulation equal to 53.06+3.47%. TEM analyses of the EVs confirmed, for morphological features and size (200-1000 nm), the good quality of the preparations. Moreover, the Authors have observed in vitro that EVs produced from osteoblasts are transferred to target cells, both in experiments in which donor cells, labelled with PHK26 (intercalating the plasma membrane) and CMFDA (cytoplasmic) fluorophores, were separated from target cells by transwells, and in experiments in which FACS-isolated EVs had been labelled and administered to unlabelled osteoblasts. Moreover, analogous preliminary experiments were carried out on RANKL KO osteoblasts (isolated from transgenic mice with RANKL deficit), in which fluorophore transfer from EVs to target cells was confirmed.

Figure 4:
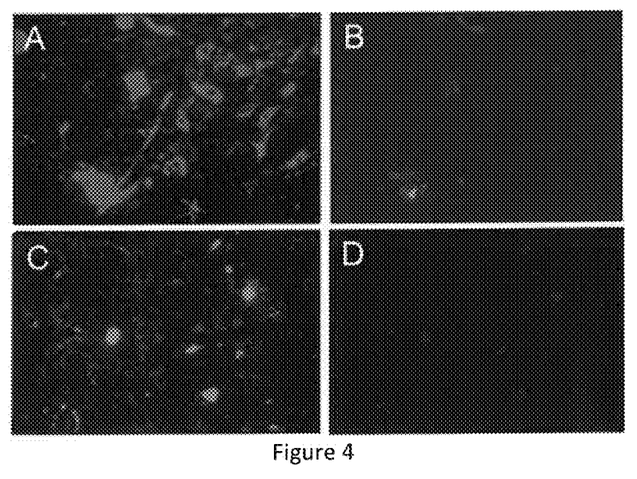
FIG. 4 shows fluorescence microscopy (20×) evaluation of osteoblasts treated for 4 days with RANKL-positive RANKL+ O-EVs stained with PKH26 (lipophilic fluorescence) (A) and CMFDA (cytoplasmic fluorescence) (B). The same cell culture maintains the staining after detachment in trypsin/EDTA and replating, (C) and (D). Representative results of 3 independent experiments.
Figure 5:
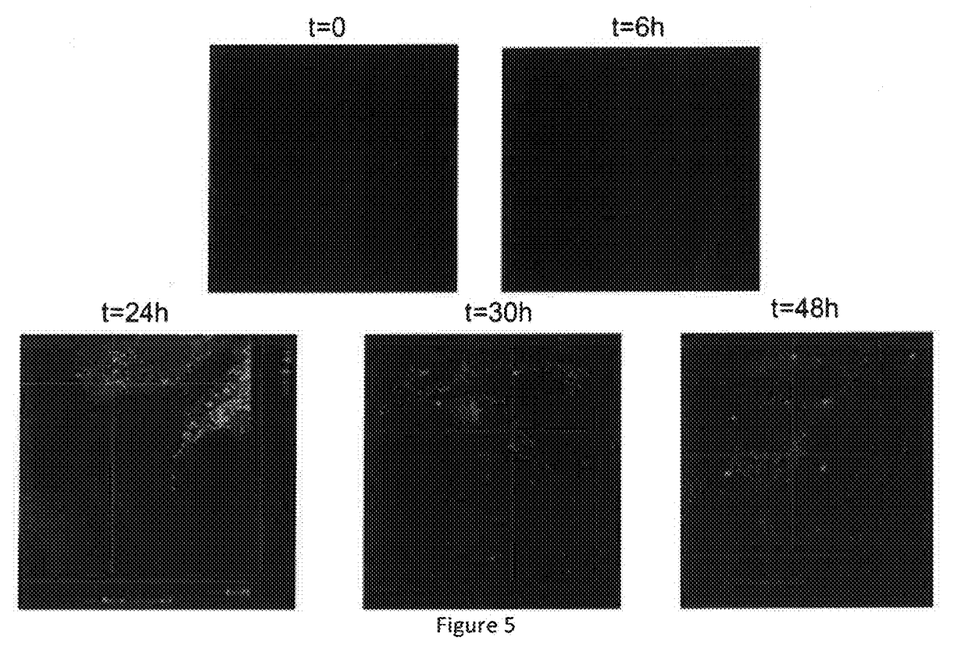
FIG. 5 shows a FACS evaluation over time of the integration kinetics in wild-type osteoblasts of RANKL+ O-EVs isolated as previously described and labelled with PKH26 and CMFDA.

The Authors have also studied EV impact on osteoclastogenesis in vivo, by treating 4-day old RANKL KO mice with intraperitoneal injections of various doses (30,000/, 60,000/, 120,000/mouse) of RANKL-positive EVs, on alternate days for 5 times. Histochemical evaluation of glycol methacrylate-included tibia revealed cells positive to the osteoclast-specific Tartrate-Resistant Acid Phosphatase (TRAcP) enzyme, which were totally absent in control RANKL KO mice. The total number of TRAcP-positive cells did not differ between various treatments with EVs (FIG. 4A). Instead, a significant dose-dependent increase in size (FIG. 4B) of the TRAcP-positive cells in mice treated with 120.000 EV, compared to mice treated with 60.000 and 30.000 EV, was evident, suggesting an increase of osteoclastogenic potential at the higher doses.

Figure 2:
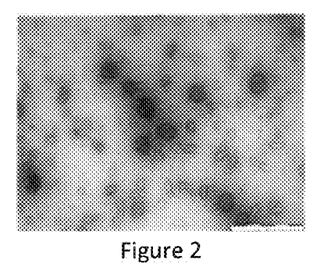
FIG. 2 shows a transmission electron microscope (TEM) evaluation of FACS-isolated O-EVs as described in FIG. 1.
Figure 3:
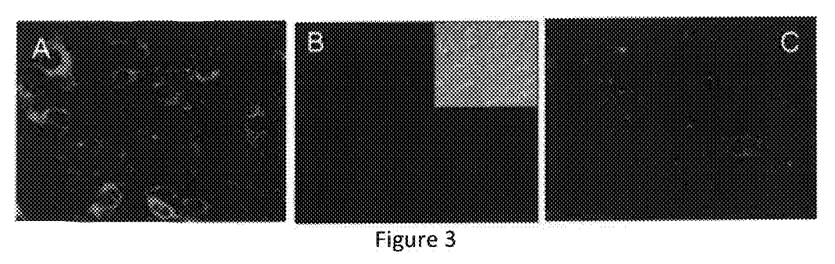
FIG. 3 shows a microscope (20×) evaluation of PKH26-labelled osteoblasts (A) cultivated in the top part of a transwell culture system (porous membrane with 1-μm Ø pores), non-stained osteoblasts in culture alone (insert: phase contrast) (B), and previously non-stained osteoblasts cultivated in the bottom of the transwell system, turned PKH26-positive after 2 days of co-culture with PKH26-labelled osteoblasts placed in the top compartment of the transwell system (C). Representative results of 3 independent experiments.
Figure 13:
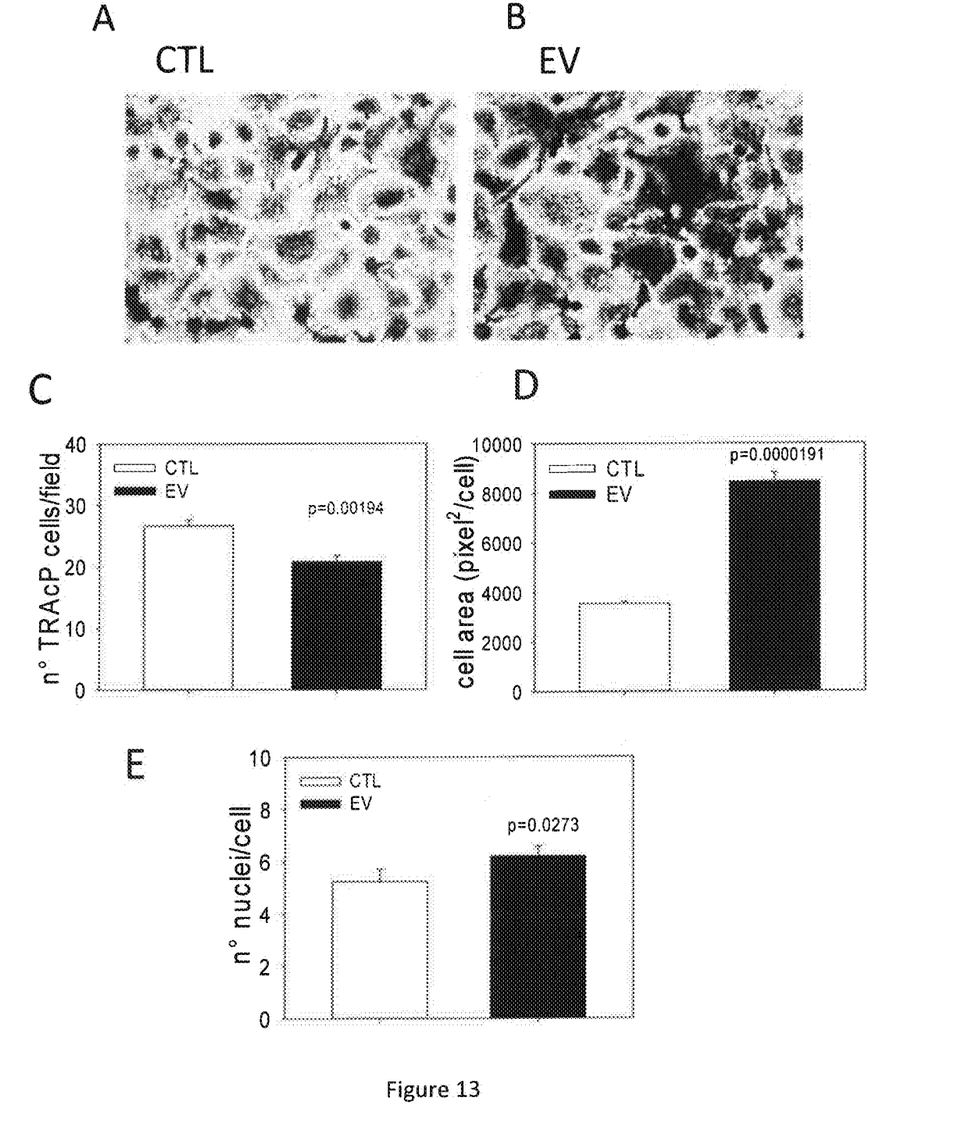
FIG. 13 shows the cytochemical evaluation by colouring of the osteoclast specific enzyme tartarate resistant acidic phosphatase TRAcP of mouse osteoclasts treated with (A) vehicle (PBS) and (B) EV isolated from osteoblasts. Follows the morphological evaluation of osteoclast parameters: (C) number of TRAcP positive cells, (D) surface of the cells counted in (C), (E) average number of nuclei per cell.

To evaluate EV integration with bone tissue, the Authors have also carried out organ cultures of whole murine parietal bones, which recapitulate bone remodelling features both in the cellular component and in the extracellular one. Therefore, parietal bones collected from RANKL KO mice were treated for 1 week with PKH26-labelled EVs. At the end of the treatment, their integration with target tissue was evaluated by confocal microscopy. The analysis (FIG. 2A-B) demonstrated that EVs had effectively integrated with bone tissue. Furthermore, a direct action of the O-EVs on in vitro mature osteoclasts has been confirmed (FIG. 13 A-E).

Furthermore, the use of the EVs of the invention (RANKL+ O-EVs) for the treatment of bone tumours was examined. Osteosarcoma is a solid tumour typical of pediatric age, with an incidence of 5 cases/year per million of subjects in the 0-19 year age bracket, constituting 2.4% of all pediatric tumours. It is deemed to generate owing to an aberrant alteration of the osteoblast, the bone matrix-depositing cell. The treatment of choice is surgical removal, oft-times resolving in amputation of the affected region. Unfortunately, despite resorting to such a debilitating treatment, the 5-year survival rate for stage III patients is only 30%. The tumour shows a good response to chemotherapeutic treatment with Doxorubicin, ifosmamide and other chemotherapeutic agents, however the incidence of recurrence and metastases, above all pulmonary ones, is high. Moreover, these chemotherapeutic agents induce significant side effects, often very severe ones, high cardiotoxicity included. In numerous tumour forms, EV participation in paracrine communication between neoplasia and organism has been observed. Moreover, EVs are turning out to be a new model of drug delivery system, and numerous studies have demonstrated EV ability to carry drugs following biotechnological manipulations. It was therefore demonstrated that RANKL+ O-EVs can carry antiblastic (antineoplastic) drugs with high efficiency inside osteosarcoma cell lines, remarkably enhancing the effect of the drug.

In the present description it is demonstrated (Example 3 and related figures) that osteosarcoma tumour U2-OS cells are able to communicate in vitro with bone tissue cells (osteoblasts, monocytes, endothelial cells) and vice versa, via EVs. Therefore, the anti-tumour properties of EVs according to the invention on U2-OS cells were evaluated. Comparison with a standard Doxorubicin (1 µM) treatment showed that the power of the EV-encapsulated drug was 100-fold higher than that of the free drug, confirming that EVs are able to carry the chemotherapeutic drug in a very efficient way.

As to targeting specificity (i.e., the ability to selectively concentrate the drug in target cells) the Authors of the invention have demonstrated (Example 4 and related figures) that labelled RANKL+ O-EVs systemically injected in mice exhibit a high and early peak of concentration in bone tissue.

The Authors of the present invention have therefore demonstrated that the RANKL+ O-EVs of the invention are able to intervene in cell phenomena that regulate bone metabolism, and to influence bone cell formation and function. Moreover, the Inventors have discovered that, by exploiting RANKL+ O-EV properties, it is possible to modify pathological functions intrinsic to bone tissue, demonstrating a highly specific therapeutic potential of RANKL+ O-EVs. Therefore, RANKL+ O-EVs can be advantageously used as carrier of anti-tumour drugs, both for primitive bone tumours, particularly osteosarcoma, and for tumours metastasized to bone. Moreover, RANKL+ O-EVs can be used to specifically carry inside the osteoblast and the osteoclast cytokines and drugs for the treatment of bone metabolism disorders. In particular, it was observed that RANKL+ O-EVs have a marked osteotropism in vivo. As demonstrated by confocal microscopy in parietal bone organ cultures, RANKL+ O-EVs are captured (uptaken) and integrated in bone tissue, in support of an advantageous use thereof in the specific therapy of skeletal diseases.

The bone pathologies according to the present description can therefore be, without however wishing to limit the invention: pathologies caused by bone metabolic alterations, primitive bone tumours, bone tumours metastases, bone metastases of tumours originated in other organs or tissues.

In one embodiment of the present invention, the pathologies caused by metabolic alterations can be diseases caused by a genetic deficiency, by the deficit of a specific protein, or in all diseases in which bone metabolism is altered, such as, by way of example and not for limitative purposes, osteoporosis and osteopetrosis.

According to a further embodiment of the invention, RANKL+ O-EVs can be used for the treatment of bone tumours, such as, e.g., primitive bone tumours, bone tumours metastases, bone metastases of tumours originated in other organs or tissues. A non-limiting example of primitive bone tumours according to the invention comprises osteosarcoma, chondrosarcoma and Ewing's sarcoma.

As mentioned above, the vesicles of the invention can be used for the treatment of bone tumours metastases and bone metastases of tumours originated in other organs or tissues such as the breast, lung or prostate.

As described herein, the RANKL+ O-EVs of the invention can be used as such, or can be loaded with therapeutic agents that could be inside said vesicles and/or on their surface.

The demonstrated osteotropicity of the vesicles of the invention, their demonstrated ability to integrate with bone tissue and their demonstrated efficiency of release of the therapeutic agent in the site of interest (with an entailed decrease even of a factor 100 in the amount of therapeutic agent required) make the RANKL+ O-EVs of the invention extremely effective and selective carriers of drugs.

The therapeutic agents according to the present description can be chemical compounds, such as, e.g., drugs active on bone metabolism (e.g., bisphosphonates), biological molecules with therapeutic activity (e.g., siRNAs, miRNAs, anti-miRNAs, shRNAs, etc., antibodies, antibody fragments recognising specific epitopes), anti-tumour drugs, comprising anti-tumour drugs for polychemotherapy (e.g., tyrosine kinase inhibitors), radiotherapy drugs, antibiotics, such as semisynthetic penicillins, quinolone antibiotics and aminoglycosides.

In case of pathologies caused by metabolic alterations, like, e.g., alterations of the RANKL/RANK/OPG system, RANKL+ O-EVs produced from healthy cells (as in the case demonstrated for osteopetrosis) which compensate for deficiencies present in cells of the diseased subject, can suffice.

Optionally, the RANKL+ O-EVs could also be loaded with therapeutic agents assisting the activity of RANKL+ O-EVs from healthy cells.

Alternatively, in case of other pathologies, such as, e.g., osteoporosis, the vesicles can be loaded with one or more therapeutic agents. By way of example and without wishing to limit the invention, said therapeutic agents can be selected from agonists of the estrogenic receptor such as Raloxifene, Lasoxifene, Bazedoxifene; Bisphosphonates, such as alendronate or Ibandronic acid, ibandronate, zoledronic acid.

In case of treatment of tumours or their metastases, the RANKL+ O-EVs of the invention could be loaded with suitable chemotherapeutic agents. A non-limiting example of said chemotherapeutic agents comprises Mifamurtide, Carboplatin, Cisplatin, Cyclophosphamide, Doxorubicin, Epirubicin, Etoposide, Ifosfamide, Methotrexate, Leucovorin or combinations thereof.

Always for the treatment of tumours or their metastases, the RANKL+ O-EVs of the invention can be loaded with radiotherapy agents. A non-limiting example of said agents comprises Radium-223 dichloride.

According to an embodiment applicable to all extracellular vesicles (O-EVs) described hereto, said vesicles can be subjected to a sterilization process which does not alter their biological properties, such as, e.g., an ultrafiltration step through membranes with a cutoff of about 0.22 μm.

The invention also relates to a pharmaceutical composition comprising extracellular vesicles isolated from osteoblastic lineage cells, optionally immortalised, as described in any one of the embodiments provided in the present description, and at least one pharmaceutically acceptable carrier for use in the therapeutic treatment of bone pathologies.

Said compositions will be suitable for therapeutic use for any of the above-described bone pathologies, therefore said compositions are to be understood for use in the treatment of pathologies caused by bone metabolic alterations, primitive bone tumours, bone tumours metastasis, bone metastasis of tumours originated in other organs or tissues. In one embodiment of the compositions according to the present invention, said pathologies caused by metabolic alteration can be diseases caused by a genetic deficiency, a deficit of a specific protein, or diseases in which bone metabolism is altered, such as, by way of example and not for limitative purposes, osteoporosis and osteomalacia.

According to a further embodiment, said compositions can be used for the treatment of primitive bone tumours, bone tumours metastases, bone metastases of tumours originated in other organs or tissues.

A non-limiting example of primitive bone tumours according to the invention comprises osteosarcoma, chondrosarcoma and Ewing's sarcoma.

As mentioned above, the compositions of the invention can be used for the treatment of bone tumours metastases and bone metastasis of tumours originated in other organs or tissues such as the breast, lung or prostate.

As described herein, the compositions of the invention can comprise RANKL+ O-EVs not loaded with therapeutic agents and/or RANKL+ O-EVs loaded with therapeutic agents that could be inside said vesicles and/or on their surface.

The therapeutic agents with which the RANKL+ O-EVs comprised in the pharmaceutical compositions of the present description are loaded can be chemical compounds, such as, e.g., drugs active on bone metabolism (e.g., bisphosphonates), biological molecules with therapeutic activity (e.g., siRNAs, miRNAs, anti-miRNAs, shRNAs, etc., antibodies, antibody fragments recognizing specific epitopes), anti-tumour drugs comprising anti-tumour drugs for polychemotherapy (e.g., tyrosine kinase inhibitors), radiotherapy drugs.

By way of example and without wishing to limit the invention, said therapeutic agents can be selected from agonists of the estrogenic receptor such as Raloxifene, Lasoxifene Bazedoxifene; Bisphosphonates, such as alendronate, Ibandronic acid, ibandronate, zoledronic acid for compositions for the treatment of osteoporosis.

In case of treatment of tumours or their metastases, the compositions of the invention could comprise RANKL+ O-EVs loaded with suitable chemotherapeutic agents. A non-limiting example of said chemotherapeutic agents includes Mifamurtide, Carboplatin, Cisplatin, Cyclophosphamide, Doxorubicin, Epirubicin, Etoposide, Ifosfamide, Methotrexate, Leucovorin or combinations thereof.

Always for the treatment of tumours or their metastases, the compositions of the invention could comprise RANKL+ O-EVs loaded with radiotherapy agents. A non-limiting example of said agents comprises Radium-223 dichloride.

In one embodiment, the pharmaceutical compositions of the invention could comprise RANKL+ O-EVs loaded with different therapeutic agents in different proportions, so as to be able to carry plural drugs by using, substantially, a cocktail of RANKL+ O-EVs.

The high effectiveness of the RANKL+ O-EVs of the invention allows to carry out pharmaceutical compositions enabling a targeted therapy, with optimization of the therapeutic effectiveness, reduction of the dosage of therapeutic agent/s and entailed reduction of side effects caused thereby. The results of the studies carried out in vitro allow to envisage a possible reduction of dose of active principles that can range from 10- to 100-fold, depending on the administration pathway, systemic or local, the therapeutic agent used, and the patient's state of health, weight, gender and age.

According to an embodiment applicable to all of the above-described compositions, the vesicles or the compositions can be subjected to a sterilization process which does not alter their biological and pharmacological properties, like, e.g., an ultrafiltration step through membranes with a cutoff of about 0.22 μm, before being introduced in the composition of the invention.

The pharmaceutical compositions of the invention could be in a form suitable for administration by intravenous, intra-arterial, localized or transmucosal injection.

The technician in the field will know which carriers and optional excipients, preservatives, etc., to use in the formulation of pharmaceutical compositions comprising the vesicles of the invention.

The invention also relates to a process for the preparation of extracellular vesicles isolated from osteoblastic lineage cells, optionally immortalised, comprising the following steps:

a. culturing osteoblasts or immortalised osteoblastic cells
b. collecting the extracellular vesicles produced by the cultured cells by ultrafiltration and/or ultracentrifugation
c. selecting the RANKL+ EVs.

The selection of the RANKL+ EVs can be carried out by any procedure known to the skilled person, such as FACS or immunomagnetic methods. In the examples below conventional methods used by the author of the invention for the selection of RANKL+ vesicles are reported.

In one embodiment, step b. of collecting vesicles could be carried out when said osteoblasts have reached a confluence of about 60%, 65%, 70%, 75%, 80%.

In a specific embodiment, the ultracentrifugation or the ultrafiltration in b. can be preceded by a pre-centrifugation at 4,000-6,000 rpm, for a time of about 10, about 20, about 30 minutes in order to eliminate cellular debris.

The ultracentrifugation in step b. of the above-described process will preferably be carried out at about 25,000, at about 30,000 or at about 35,000 rpm, for a time of from 30 to 100 minutes, like, e.g., about 30, 40, 50, 60, 70, 80, 90, 100 minutes.

In one embodiment, the ultracentrifugation could be carried out at about 30,000 rpm for a time of about 70 minutes.

In step b., the culture medium can be subjected to ultracentrifugation as mentioned above, or to ultrafiltration, to isolate the extracellular vesicles of interest.

It is also possible to carry out both steps in any possible order.

The ultrafiltration in b. according to the invention can be carried out with filters having a cutoff of from 50 to 300 kDa, like, e.g., about 50, 100, 150, 200, 250, 300 kDa. In a preferred embodiment, the cutoff can be of about 100 kDa.

In a specific embodiment, the above-described process can be carried out in bioreactors allowing to accommodate a high number of cells in three-dimensional structures and facilitate RANKL+ O-EVs isolation in a continuous flow.

Further, in order to increase RANKL+ O-EV production by the cells, the culturing in step a. can be carried out in the presence of parathyroid hormone.

Always with the goal of increasing the RANKL+ O-EVs production, the cells can be modified with genetic engineering techniques so to overexpress the cytokine by transfection of a RANKL coding vector in primary osteoblasts (by electroporation/nucleofection) or in osteogenic cell lines, MC3T3, or other immortalised osteoblast cell lines (e.g. by transfection with liposomal transfection).

According to the invention, the above-described process can comprise a step c. wherein said vesicles are subjected to ultrafiltration with 0.22 μm filters so as to obtain sterilized vesicles.

Object of the present invention are extracellular vesicles isolated from osteoblastic lineage cells, optionally immortalised, obtainable with the above-described process according to any one of its embodiments.

The invention also provides a process for loading extracellular vesicles isolated from osteoblastic lineage cells, optionally immortalised, with one or more therapeutic agents or with one or more contrast agents, comprising the steps of a. incubating said vesicles and/or osteoblastic lineage cells, optionally immortalised, in a culture medium containing said one or more therapeutic agents or one or more contrast agents
b. collecting by ultracentrifugation and/or filtration and/or ultrafiltration and/or column filtration, ultracentrifugation on sucrose gradient and/or separation with immunomagnetic methods the vesicles thus loaded, The vesicles, therefore, can be loaded directly or indirectly, as the above-described process can be applied to cultured cells or to vesicles already isolated.

In case the desired therapeutic agents be unable to easily penetrate the cells or the vesicles themselves, the above-described process can be optimized by introducing an electroporation step y. prior to or concomitantly with step a.

The therapeutic agent is as defined in the above description and comprises chemotherapeutic agents, siRNAs, miRNAs, anti-miRNAs, constructs for transient transformation, pharmacological molecules or mixtures thereof, antibodies or other therapeutic biological molecules. Alternatively, the invention provides a process for loading extracellular vesicles isolated from osteoblastic lineage cells, optionally immortalised with one or more therapeutic agents, comprising the steps of a. transforming osteoblastic lineage cells, optionally immortalised, so to express a therapeutic agent of interest,
b. culturing osteoblasts or immortalised osteoblastic cells of the osteoblastic lineage, optionally immortalised, transformed in step a.,
c. collecting by ultracentrifugation and/or filtration and/or ultrafiltration and/or column filtration, ultracentrifugation on sucrose gradient and/or separation with immunomagnetic methods the vesicles thus loaded and selecting RANKL+ EVs.

As to the contrast agents that can be used in the above-described first process of loading the vesicles, i.e. that related to loading with contrast agents, said contrast agent is any one means that normally can be used by in vivo diagnostic imaging techniques.

The vesicles loaded according to the above-described process can be loaded with means suitable for diagnostic imaging carried out by ionizing radiations (e.g., conventional radiology, computerized axial tomography), by scintigraphy or by nuclear magnetic resonance.

According to one embodiment, said contrast agent contains an X-ray opaque iodate compound.

According to another embodiment, said contrast agent contains or consists in a radioactive isotope for scintigraphy.

Without wishing to limit in any way the invention, said isotope can be, for instance, selected from 99m technetium, iodine 131, thallium 201, iodine 125 and other isotopes commonly used for diagnostic purposes by the technician in the field.

According to another embodiment, said contrast agent is a contrast agent for nuclear magnetic resonance, such as, e.g., a contrast agent containing gadolinium chelated compounds.

Object of the invention are also extracellular vesicles isolated from osteoblastic lineage cells, optionally immortalised, obtainable by any one of the above-illustrated processes.

Given their ability to recognise and concentrate specifically in osteoblastic lineage cells, object of the invention is also the use of extracellular vesicles isolated from osteoblastic lineage cells, optionally immortalised, loaded with suitable contrast agents, such as for instance described above, in imaging techniques for the study of bone pathologies wherein said RANKL+ O-EVs can be used as biological markers, e.g. to single out primitive or occult metastatic tumours.

As stated above, according to the invention, it is possible to genetically modify the starting cell lines, from which the vesicles of the invention are isolated, so to increase the RANKL expression in the same. This modification may be carried out by conventional genetic engineering techniques without the need of particular experimentation by the skilled person.

Object of the invention is also a diagnostic method, by imaging, for the diagnosis of bone pathologies, comprising the steps of administering to a patient the vesicles of the invention loaded with contrast agents or radioactive molecules (e.g. technetium) or with stable isotopes (e.g. deuterium or C13) for imaging techniques, systemically (e.g., intravenously);

detecting the body distribution, or the distribution in specific sites of interest, of said vesicles and processing it by imaging techniques.

Given the property of RANKL+ O-EVs of concentrating in osteoblastic lineage cells, comprising the tumour cells deriving from said lineage, and in tumour cells metastasized to bone, the above-described process can provide morphofunctional information on bone architecture, on the presence of primitive or secondary tumours (metastases) and on the presence of bone tumours metastases in other organs and tissues.

Both of the above-described processes could further comprise an ultrafiltration step c. with 0.22 μm filters.

Therefore, the invention also relates to extracellular vesicles isolated from osteoblastic lineage cells, optionally immortalised, loaded with one or more therapeutic agents obtainable according to the above-described processes in any embodiment thereof.

Lastly, object of the invention is a therapeutic method for the treatment of bone pathologies, comprising the administration of therapeutically effective amounts of extracellular vesicles isolated from osteoblastic lineage cells, optionally immortalised, optionally loaded with one or more therapeutic agents, or of a cocktail of said vesicles, to a subject in need thereof.

As indicated above, said subject may be any animal having a bone endoskeleton, in particular a mammalian, in particular a human being.

The bone pathologies are as defined above, and the vesicles could be loaded or not loaded with therapeutic agents in the ways and with the therapeutic purposes defined above.

The therapeutic method of the invention also provides the administration of cocktails of RANKL+ O-EVs according to the present description.

According to all of the above-described embodiments, related to the vesicles of the invention, the compositions, the processes, the therapeutic methods, said osteoblastic lineage cells, optionally immortalised, originate from the same species that has to be treated and can be autologous or allogenic. Therefore, in case of human beings said cells will be of human, autologous or allogenic origin.

In the therapeutic method of the invention the composition could be administered to the patient intravenously, intra-arteriously, intranasally or in a local direct way. The effective dosage could be evaluated by the attending physician on an empirical basis, or set by in vivo evaluation for each pathology.

MATERIALS, METHODS AND EXAMPLES

1. Osteoblast Culture

Primary murine osteoblasts are isolated from parietal bones of 7-10 day old CD1 mice. Litter is kept and controlled according to the provisions of the law, under supervision of a veterinary in charge. When needed for the experiments, animals are sacrificed according to standards and parietal bones explanted. After soft tissue removal, bones are subjected to enzymatic digestion by successive passes in an extraction solution comprised of bovine trypsin (25 mg/ml) and collagenase IV (10 ml/ml) in HANKS' solution and kept under stirring at 37° C. Obtained cells are blended, considered as osteoblast-enriched culture and used for the experimental purposes. Osteoblastic phenotype is routinely evaluated by biochemical assay of alkaline phosphatase positivity on a cell aliquot fixed in PFA/PBS (4% v/v).

1.1 Detail of Isolation Methodology of RANKL+ O-EVs from Culture Medium

Murine osteoblasts, obtained as previously described, are plated in 150 cm$^2$ culture flasks and grown in DMEM culture medium containing glutamine (5 mM), penicillin (1 mg/ml), streptomycin (2 mg/ml) and American fetal bovine serum (10% v/v) (FBS), and kept in incubator under 5% $CO_2$. Upon reaching 70% confluence, cells were abundantly washed with PBS (3 times) to remove serum residues, and kept 24 hours in glutamine (5 mM)/penicillin (1 mg/ml), streptomycin (2 mg/ml) DMEM medium.

Thereafter, culture medium is centrifuged at 5,000 RPM to remove any cellular debris, for 20 min at 4° C., then supernatant is collected, poured into sterile ultra-centrifuge tubes, and centrifuged at 30.000 RPM, for 70 minutes at 4° C.

At the end of the procedure, the pellet obtained is resuspended in 500 ml PBS and incubated with 10 microM CMFDA, at 37° C. for 30 min. The pellet is then brought to maximum volume with PBS in ultra-centrifuge tube, centrifuged at 30,000 RPM for 70 minutes at 4° C., and evaluated for quantity and quality by cytofluorimetric analysis. The RANKL expressing O-EVs are isolated by FACS or by immunomagnetic methods. According to experimental needs, the vesicle pellet is also incubated with PKH26 (5 microM, Sigma-Aldrich) for 30 minutes at 37° C. and subsequently centrifuged at 30,000 RPM for 70 minutes.

1.2. Osteoclasts Culture

Primary mouse osteoclasts are obtained by medullar macrophages differentiation isolated from CD1 long bones of age comprised within 7-10 days. The litter is kept and maintained according to the legal requirements, under the supervision of a veterinary responsible. When experimentally needed, the animals are sacrificed according to the laws and the long bones are explanted and cleaned from soft tissues. The bones are then submitted to mechanical disruption in order to free the bone marrow. The cells obtained are diluted in PBS and stratified 1:1 on Histopaque (Sigma-Aldrich), and centrifuged for 30' at 450 g. The formed buffy coat is collected and washed with PBS. The cells thus obtained are plated on Petri dish for 12 minutes in order to eliminate the stromal cellular contaminant. The non-adhering cells are then collected and plated at a 1200000 cells/cm$^2$ density, adding h M-CFS (50 ng/ml) (Peprotech) for 3 days and subsequently adding for other 3 days h M-CSF (50 ng/ml) (Peprotech) and h RANKL (120 ng/ml) (Peprotech). At the end of the treatment the cells are detached by tripsin/EDTA and re-plated at a density of di 50.000 cellule in 96 multiwell plates. This culture is considered as enriched in mature osteoclasts and is used for the following experimental purposes. The osteoclastic phenotype is routinely assessed by biochemical assay to tartarate resistant acidic phosphatase positivity on a cell aliquot fixed in PFA/PBS (4% v/v).

2. Experimental Protocol 2.1 Cytofluorimetric Analysis

FACScanto II (BD Biosciences) was resorted to for cytofluorimetric analysis. Prior to each evaluation session, the instrument was calibrated making use of commercial microbeads (Spherotech) of known size (0.25-0.52-0.73-1.25 micrometres) to identify the dimensional limits to be used for sample enrichment. Moreover, the prescribed fluorescence channel compensations are carried out. Following preparation of the analytical instrument, the vesicle pellet is enriched in intact CMFDA positive structures, dimensionally compatible with parameters indicated in the literature ($\leq 1$ μm). The extracellular vesicle population obtained is subsequently used for further investigations.

For evaluation of RANKL expression, CMFDA positive RANKL+ O-EV pellet is incubated for 30 min with mouse anti-RANKL antibody conjugated with Phycoerythrin (PE) (1:100) in PBS/BSA (1%). RANKL+ O-EVs are then FACS analysed and CMFDA/PE double-positive fraction is isolated for further evaluations.

2.2 In Vivo Effect

Figure 7:
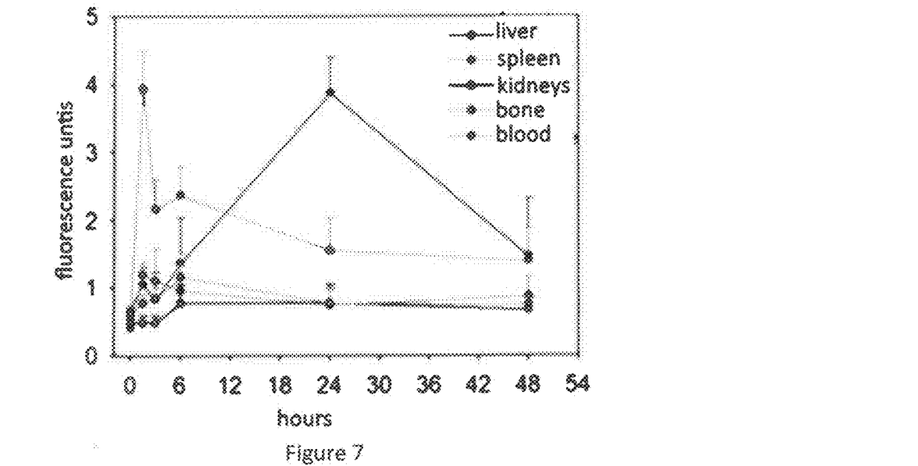
FIG. 7 shows the fluorimetric analysis (excitation wavelength 550 nm; emission wavelength 567 nm) of the lipid fraction extracted from indicated tissues of 5-day old CD1 mice inoculated with PKH26-stained RANKL+ O-EVs.

RANKL+ O-EVs appropriately isolated, as indicated above, are injected intraperitoneally (i.p.) in 4-day old wild-type (wt) or RANKL KO animals. For evaluation of tissue distribution (FIG. 7) in wt animals, 30,000 RANKL positive EVs are administered intraperitoneally. For the osteocalceogenic effect in RANKL KO animals, 30,000-60,000-120,000 Rankl positive EVs are administered i.p. every 2 days, for a total of 5 times.

2.3 Extraction and Evaluation of PKH26 Content from Tissue

For the spectroscopic measurement of tissue-accumulated PKH26, following i.p. administration the lipid component of tissue was extracted. For this purpose, an extraction procedure by methanol/chloroform was used, according to a 0.8:2:1 (sample:methanol:chloroform) relative ratio.

For liver, spleen, kidney and bone (femurs and tibias) the whole organ was mechanically homogenized in PBS before the step in methanol, whereas 50 μl of whole blood were directly blended to methanol according to the indicated ratio. The final chloroform phase is concentrated in speed vacuum centrifuge to total evaporation of the solvent. Lastly, the sample is resuspended in 100 μl of chloroform. The extract is thus read by fluorimetric analysis (excitation wavelength: 550 nm; emission wavelength: 567 nm)

2.4 TEM Analysis

The suspension of FACS-isolated RANKL+ O-EVs (5 μl) is fixed with 4% PFA (1:1) and then placed on a Formvar-coated grid, counterstained with uranyl acetate, and then observed using a FEI/Philips CM-100 transmission electron microscope.

2.5 Statistical Analysis

Statistical analysis is conducted by Student's t test. Data are considered statistically significant with a value of $p<0.05$.

Figure 1:
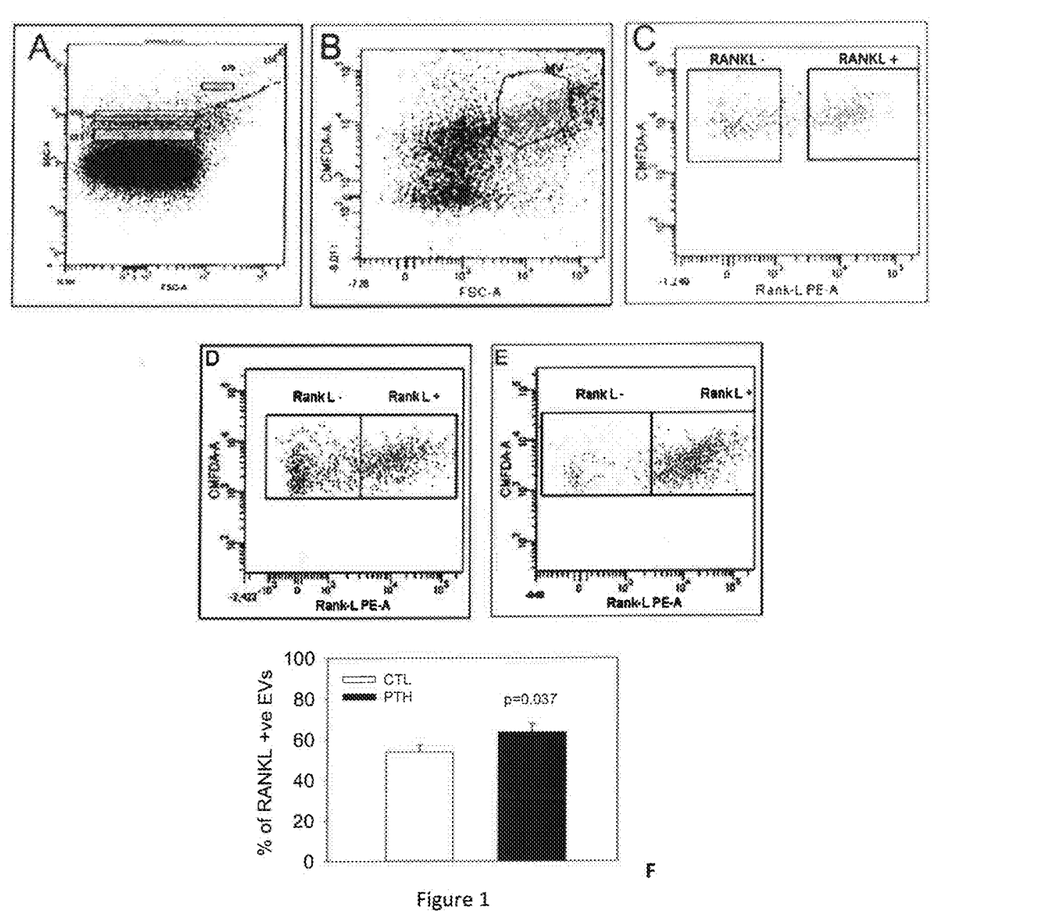

Example 1. RANKL+ O-EVs Expose RANKL and are FACS-Identifiable and FACS-Separable RANKL+ O-EVs isolated by ultracentrifugation from primary osteoblast conditioned medium were incubated with anti-RANKL antibodies conjugated with Phycoerythrin and subjected to cytofluorimetric analysis. The presence of a RANKL-positive RANKL+ O-EV subpopulation equal to 53.06+3.47% was observed (FIG. 1C). This fraction was increased by subjecting osteoblasts to parathyroid hormone stimulation (FIG. 1D-E) reaching values of 63.6±4.20% (p=0.037).

Figure 8:
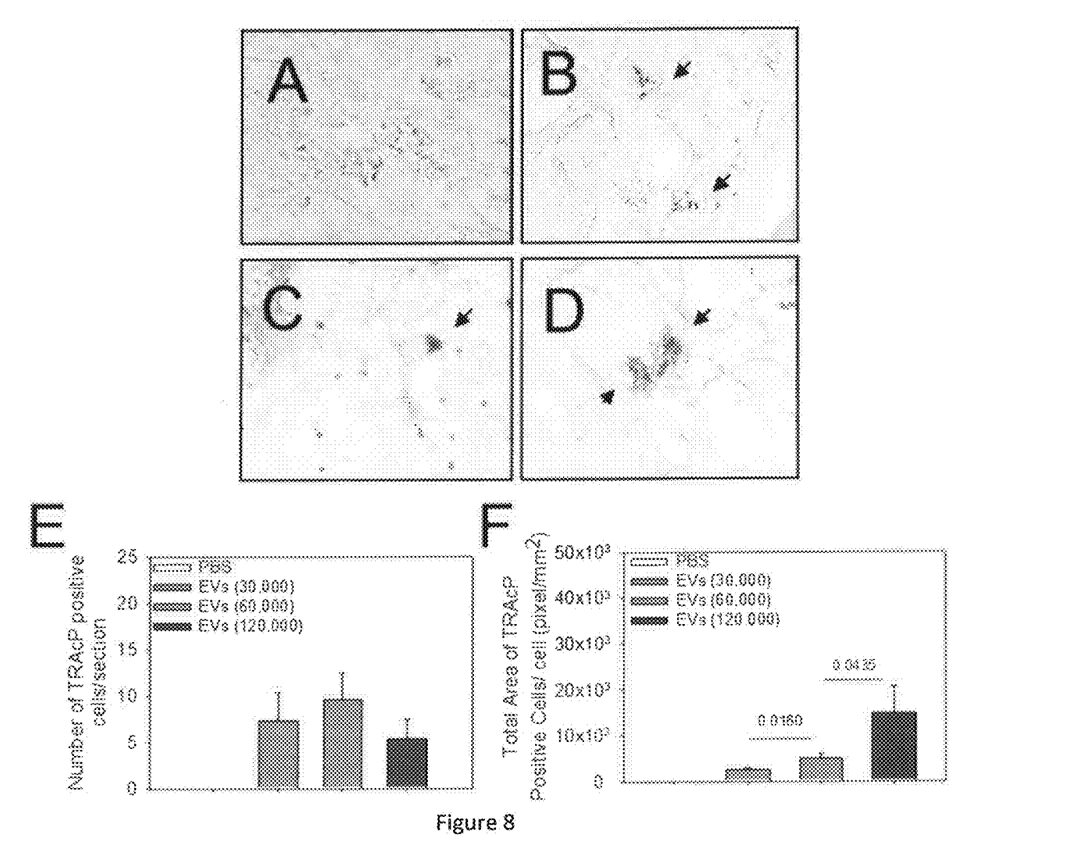
FIG. 8 shows the histological (40×) evaluation by TRAcP staining of tibial sections of RANKL KO mice treated with (A) PBS or (B) RANKL-positive RANKL+ O-EVs. Arrows indicate TRAcP-positive cells of the osteoclastic line.

Example 2. RANKL-Positive RANKL+ O-EVs Exhibit Osteoclastogenic Activity In Vivo and Ex Vivo 4-day old mice with congenital RANKL deficit (therefore lacking osteoclastic activity) were treated with i.p. injections of different doses (30,000/, 60,000/, 120,000/mouse) of RANKL-positive RANKL+ O-EVs, on alternate days, for 5 times. Histological evaluation of bone marrow of glycol methacrylate-included tibia revealed TRAcP-positive cells, index of osteoclastic activity, which were totally absent in RANKL KO control mice (FIG. 8A-D). The total number of TRAcP-positive cells was not different between the different treatments with EV (FIG. 8E). Instead, a significant dose-dependent increase of the total area (FIG. 8F) of TRAcP-positive cells was evident in mice treated with 120,000 EVs compared to mice with 60,000 and 30,000 EV treatments, suggesting an increase of osteoclastogenic potential at higher doses.

Figure 6:
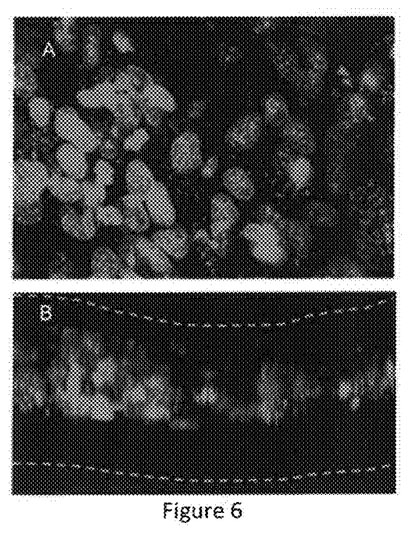
FIG. 6 shows, in (A), confocal microscope (60×) evaluation of RANKL KO murine parietal bones treated ex vivo with PKH26-labelled RANKL+ O-EVs. Bright spots correspond to RANKL+ O-EV accumulations inside the cytoplasm. Hoechst-labelled nuclei are visible. (B) Reconstruction of the figure in (A) on the Z-axis.

To evaluate RANKL+ O-EV effect on osteoclastogenesis ex vivo, parietal bones of RANKL KO mice were treated for 1 week in culture with PKH26-labelled EVs. EV integration with target tissue was evaluated. Confocal microscopy analysis at the end of the treatment demonstrated that EVs had integrated with bone tissue (FIG. 6A-B).

Figure 9:
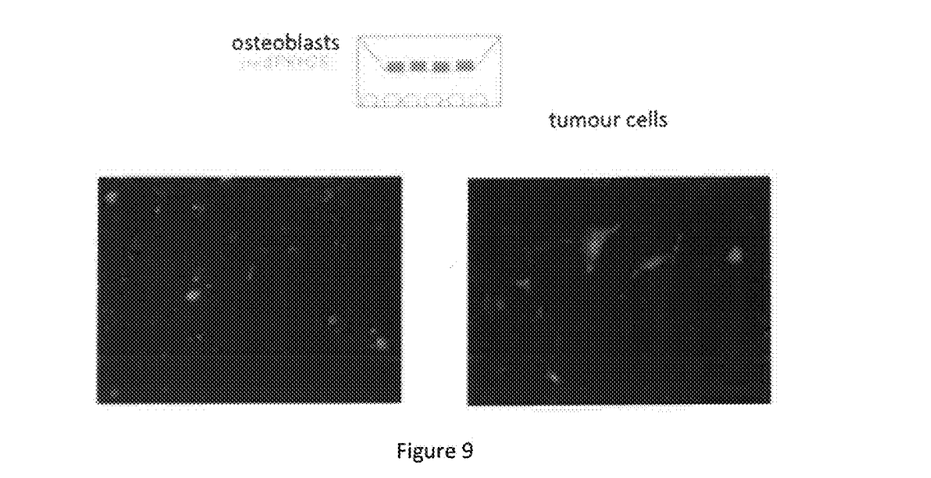
FIG. 9 shows, in A, the experimental layout of the transwell culture system (porous membrane with 1 μm-diameter pores). In B, microscope (10×) evaluation of human osteosarcoma cell lines U2O (B), and SAOS2 (C), turned red (PKH26) after 48 hours of co-culture.

Example 3: Doxorubicin-Loaded RANKL+ O-EVs Exhibit Antiblastic Activity In Vitro Two Orders of Magnitude Greater than the Free Drug Mouse osteoblasts labelled with membrane fluorescent dye PKH26, were placed in co-culture, separated by transwell (porous membrane with 1 μm Ø pores) with human osteosarcoma cell lines. FIG. 9A shows the experimental layout. Osteoblasts transfer the PKH26 dye, presumably by EVs which cross transwell pores and are captured (uptaken) by osteosarcoma cells. FIGS. 9B and 9C show a microscope analysis of human osteosarcoma cell lines (B) U2Os and (C) SAOS2 turned positive to fluorescence in the wavelength of red after 48 hour of co-culture.

Figure 10:
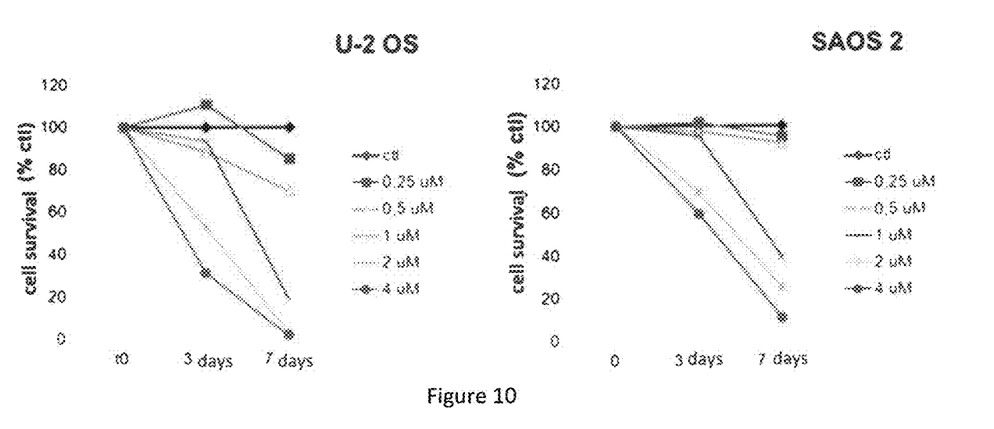
FIG. 10 shows the cell viability assay conducted with 3-(4,5-dimethylthiazol-2-yl)-2,5-diphenyltetrazolium (MTT) of human osteosarcoma lines treated with various Doxorubicin concentrations as indicated in the captions.

Osteosarcoma cell lines sensitivity to anti-tumour drug Doxorubicin was evaluated by treating the cells with different Doxorubicin concentrations and carrying out cell viability assay with MTT at different times. The results confirm that drug toxicity on tumour cells manifests itself for concentrations of >1 micromole/litre (FIG. 10).

Figure 11:
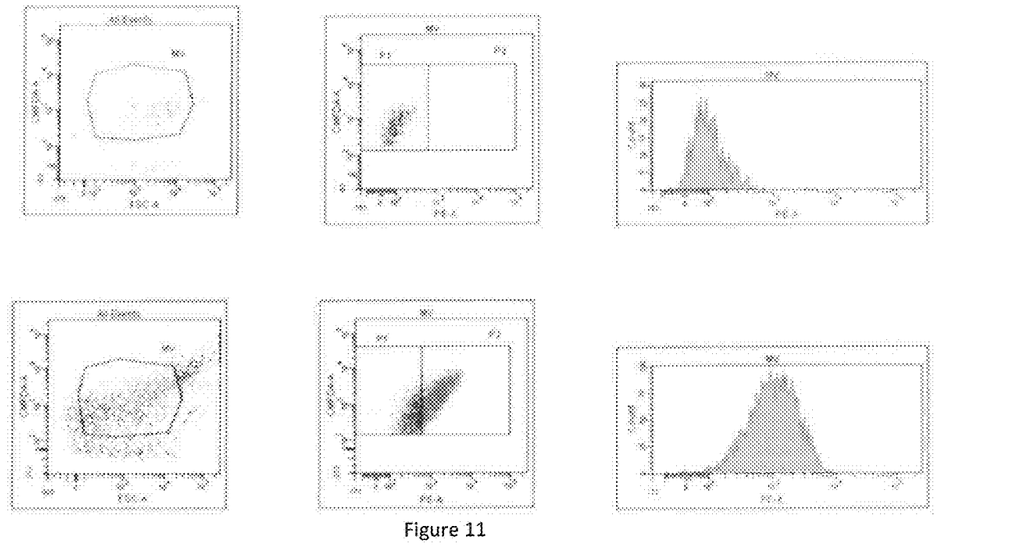
FIG. 11 shows FACS (FACScanto II—BD) evaluation of pellets of RANKL+ O-EVs isolated from osteoblast conditioned medium, incubated without or with Doxorubicin (DXR). Dot-Plot of RANKL+ O-EVs incubated with PBS (A) or Doxorubicin (300 mg/ml) (B) and evaluated for positivity to fluorescence of CMFDA and of Doxorubicin. Positivity profile of the population of FACS-isolated RANKL+ O-EVs at 570 nm (red, PE-A).

RANKL+ O-EVs were incubated with Doxorubicin (300 mg/ml) in vitro, then subjected to FACS. RANKL+ O-EV-associated doxorubicin confers red fluorescence to the nanoparticles, enabling FACS isolation thereof (FIG. 11).

Figure 12:
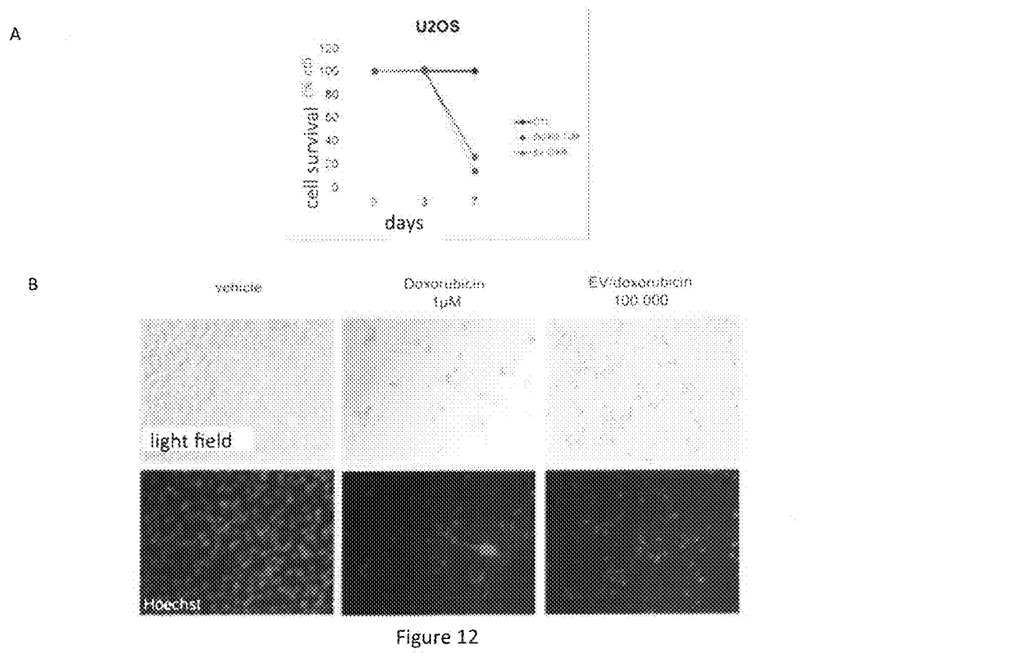
FIG. 12 shows, in A, the cell viability assay of U2OS cells up to 7 days, treated on day 0 with Doxorubicin or 100.000 EV-DXR. In B, bright-field or fluorescence microscopy analysis of the cells treated as described in A.

Human osteosarcoma cell lines were treated with free Doxorubicin (235 ng, corresponding to a concentration of 1 micromole/litre in the medium) or with RANKL+ O-EV-associated Doxorubicin (100,000 FACS-isolated nanoparticles, containing 3.2 ng of Doxorubicin, corresponding to a concentration of 10 nanomole/litre in the medium). In both cases, the treatment caused death of about 80% of the neoplastic cells (FIG. 12). However, the treatment with anti-tumour drug-loaded RANKL+ O-EVs allowed to obtain this effect with a Doxorubicin dose 100-fold lower than the free drug (Table 1 below).

| Free | EV-DXR |
|---|---|
| 235 ng | 3.2 ng |
| 1 µM | 10 nM |

Example 4: RANKL+ O-EVs Concentrate Specifically and Precociously in Bone Tissue In Vivo after Systemic Injection 5 day-old CD1 mice (n=6) were systemically (intraperitoneally) inoculated with PKH26-labelled RANKL+ O-EVs and sacrificed at different times. Samples of blood and of bone, liver, spleen and kidney tissues were collected. Tissue-extracted lipid fraction was subjected to fluorimetric analysis to detect PKH26 dye presence (excitation wavelength 550 nm; emission wavelength 567 nm). The results (FIG. 7) demonstrate an early uptake peak in bone tissue, with minimum deposition in other tissues examined. The late peak at hepatic level might be due to degradation products.

Example 6: RANKL+ O-EVs are Capable of Directly Sustaining the Osteoclast Survival and Maturation Mature osteoclasts are treated with PBS o O-EVs for 48 hours. At the end of the treatment the cells are fixed in 4% PFA (v/v) and submitted to TRAcP colouring (FIG. 13). The microscopic assessment shows, with reference to the control, an increase of intensity of the colouring of the osteoclast specific enzyme, which is an indirect parameter of a potential higher cellular activity (A-B). Further morphometric analysis (C, D, F) confirm a significantly EVs' positive pro-osteoclastic modulation.

Figure 14:
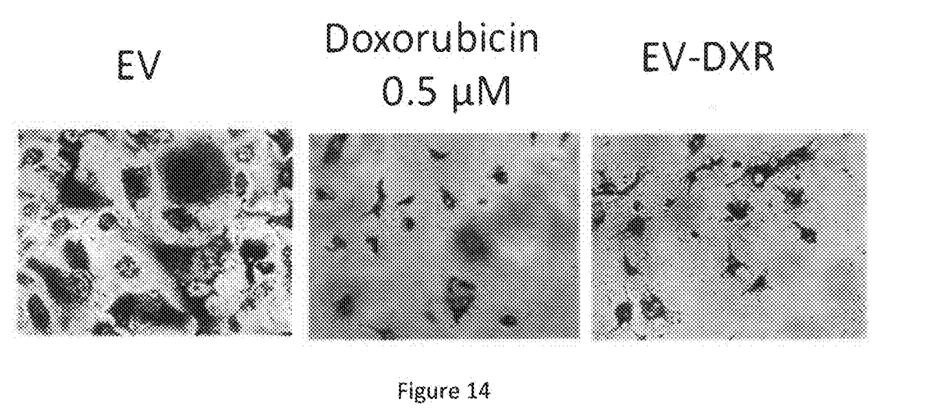
FIG. 14 shows the microscopic analysis (20×) of mature mouse osteoclasts TRAcP positive, treated as described for 48 hours with doxorubicin or EV-DXR.

Example 6: RANKL+ O-EVs Loaded with Doxorubicin Show an In Vitro Antiosteoclast Activity in a Way Comparable to the Free Medicament The sensitivity of mature osteoclasts to the antitumor medicament doxorubicin has been evaluated by treating the cells with different doxorubicin concentrations (0.1-0.2-0.5-1-2-4 µM) and carrying out TRAcP colouring after fixing. The results confirm that the toxicity of the medicament shows for concentrations higher than 0.2 micromolar. EVs isolated from osteoblasts have been incubated with doxorubicin in vitro (300 mg/ml) for 30 minutes and after washing they have been incubated for 48 hours with mature osteoclasts. The results (FIG. 14) show an apoptotic effect of the DXR-O-EVs similar to the free doxorubicin concentration of 0.5 µM, inducing a strong detachment of the cells during the treatment and showing in any case evident signs of culture cells suffering and retraction.

Figure 15:
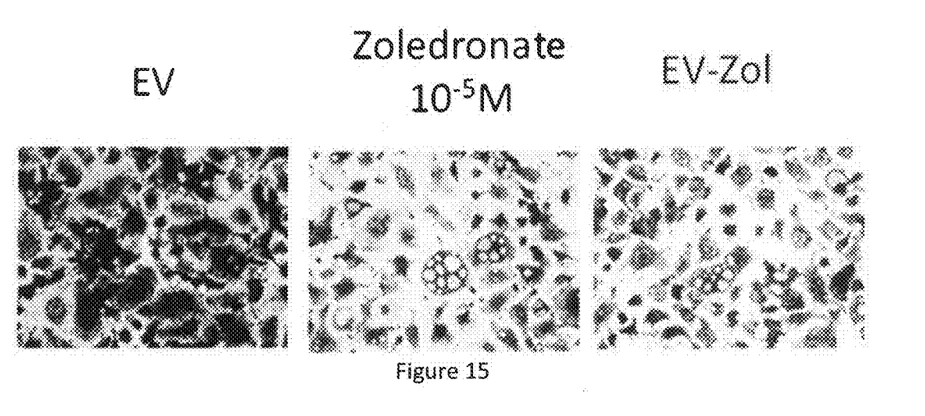
FIG. 15 shows the microscopic analysis (20×) of mature mouse osteoclasts TRAcP positive, treated as described for 48 hours with zoledronate or EV-ZOL.

Example 7: RANKL+ O-EVs Loaded with Zolentronate Exhibit an In Vitro Antiosteoclastic Activity with an Effect Comparable to the Free Medicament The sensitivity of mature osteoclasts to the medicament zolendronate has been assessed by treating the cells with different zolendronate concentrations ($10^{-8}$, $5 \times 10^{-8}$, $10^{-7}$, $5 \times 10^{-7}$, $10^{-6}$, $5 \times 10^{-6}$, $10^{-5}$, $5 \times 10^{-5}$, $10^{-4}$ M) and carrying out TRAcP colouring after fixing. The results confirm that the medicament toxicity on mature osteoclasts is shown at concentrations higher than $10^{-7}$ M. Evs isolated from osteoblasts have been incubated with zolentronate in vitro (10 mM) for 90 min at 37° C. and, after washing, they have been incubated for 48 hours with mature osteoclasts. The results (FIG. 15) show an apoptotic effect of the zol-OEVs similar to the concentration of free zol $10^{-7}$ M, inducing a massive detachment of the cells during the treatment and showing in any case, evident signs of culture cells suffering and retraction.

The invention claimed is:

1. Loaded extracellular vesicles isolated from osteoblastic lineage cells, optionally wherein the cells are immortalised cells,
    wherein the vesicles comprise RANKL (Receptor Activator of NF-KB Ligand) on one or more membranes of the vesicles;
    wherein the vesicles are loaded with one or more therapeutic agents selected from the group consisting of Mifamurtide, Carboplatin, Cisplatin, Cyclophosphamide, Doxorubicin, Epirubicin, Etoposide, Ifosfamide, Methotrexate, Leucovorin, Raloxifene, Lasoxifene, Bazedoxifene, Bisphosphonates, alendronate, Ibandronic acid, ibandronate, zoledronic acid, and mixtures thereof; and
    wherein the loaded extracellular vesicles are osteotropic.

2. A pharmaceutical composition comprising the extracellular vesicles of claim 1, further comprising at least one pharmaceutically acceptable carrier.

\* \* \* \* \*